(12) United States Patent
Jackson et al.

(10) Patent No.: US 9,448,196 B2
(45) Date of Patent: Sep. 20, 2016

(54) ELECTRONICALLY CONDUCTIVE FLUID DETECTOR

(71) Applicant: Cranksaver LLC, Conroe, TX (US)

(72) Inventors: William J. Jackson, Conroe, TX (US);
Benny J. Webber, Odessa, TX (US);
Jesse J. Juarez, Houston, TX (US)

(73) Assignee: Cranksaver LLC, Conroe, TX (US)

( * ) Notice: Subject to any disclaimer, the term of this patent is extended or adjusted under 35 U.S.C. 154(b) by 111 days.

(21) Appl. No.: 14/320,947

(22) Filed: Jul. 1, 2014

(65) Prior Publication Data

US 2016/0003755 A1    Jan. 7, 2016

(51) Int. Cl.
G01R 31/02    (2006.01)
G01R 27/26    (2006.01)
G01N 27/06    (2006.01)

(52) U.S. Cl.
CPC ..................................... *G01N 27/06* (2013.01)

(58) Field of Classification Search
CPC .......................... A61B 2562/08; A61B 5/0031
USPC ................................ 324/452, 453, 693, 71.1
See application file for complete search history.

(56) References Cited

U.S. PATENT DOCUMENTS

| | | | |
|---|---|---|---|
| 2,420,177 A | 5/1947 | Krall | |
| 2,716,165 A | 8/1955 | Pfitzner | |
| 3,728,897 A | * 4/1973 | Wallman | G01F 23/263 73/304 C |
| 3,876,935 A | 4/1975 | Guillermie | |
| 4,266,195 A | 5/1981 | Keefner et al. | |
| 4,304,132 A | 12/1981 | Snaper | |
| 4,410,885 A | 10/1983 | Stenstrom | |
| 4,728,924 A | 3/1988 | Franklin | |
| 4,878,043 A | 10/1989 | Heusquin et al. | |
| 4,926,818 A | 5/1990 | Oppenheim et al. | |
| 8,105,483 B2 | 1/2012 | South et al. | |
| 2004/0212375 A1 | 10/2004 | Marszalek | |

FOREIGN PATENT DOCUMENTS

GB    2408803    6/2005

OTHER PUBLICATIONS

International Search Report and Written Opinion for Application No. PCT/US2015/038850 dated Oct. 19, 2015.

* cited by examiner

*Primary Examiner* — Vincent Q Nguyen

(74) *Attorney, Agent, or Firm* — Tumey L.L.P.

(57) ABSTRACT

A sensor detects the presence of an electrically conductive liquid such as water or the material at the bottom of a reservoir such as an oil pan or crank case. The water or other material will enter a gap between two contacts that are connected to a power source and a signal device such as an LED. The power source may be a battery positioned within the sensor or may be external.

5 Claims, 1 Drawing Sheet

ELECTRONICALLY CONDUCTIVE FLUID DETECTOR

BACKGROUND OF INVENTION

1. Field of the Invention

This invention is directed to a sensor that detects the presence of an electrically conductive fluid such as water and the like in a reservoir. The reservoir may normally contain a non-conductive fluid such as oil or fuel. The presence of water in the reservoir such as a crank case of an engine, an oil pan, a pump crankcase or in any device having splash or oil fed lubrication would normally indicate a problem with some component of the apparatus associated with the reservoir. Thus the sensor can provide a visual or audible indication that there is a problem with the operation of the apparatus.

2. Description of Related Art

U.S. Pat. No. 2,420,177 discloses a sensor including two contacts that are positioned at the lower portion of an oil pan. The sensor is part of an oil plug P. According to the disclosure, metallic particles that are created as a result of the failure of a part of the engine or machine will accumulate in the plug and eventually will bridge the gap between contacts 16 to cause the flow of electricity which will activate signals. U.S. Pat. No. 4,410,885 discloses a sensor 10 mounted in the oil pan of an internal combustion engine that includes an inner electrode 42 and an outer electrode 44 which is formed with a flexible helical coil. The probe is connected to an external battery 26 and warning light 22.

Both devices include several parts which may fail or become contaminated in such a way that would render them inoperative. Both also rely upon an external source of power.

BRIEF SUMMARY OF THE INVENTION

The invention disclosed and claimed herein includes a simple, easy to manufacture sensor that detects the present of an electrically conductive liquid or other material in a reservoir such as an oil pan or crank case. It may also be used in fuel filters for jet fuel to detect the presence of water in the fuel. The sensor includes an elongated relatively cylindrical hollow housing that at one end supports an indicator or signal such as a light emitting diode (LED). Also, a battery is located within the housing and serves as the power source for the LED. The other end of the housing includes a pin member that is electrically isolated from the outer housing by being located within a central bore in the other end of the housing such that a gap exists between the outer housing and the pin.

When the sensor is positioned within a reservoir, any water that accumulates at the bottom of the reservoir will enter the annular space between the pin and the outer casing which will complete the electrical circuit causing the light or other indicator to be activated.

In an alternate embodiment of the invention, the internal battery may be eliminated and the outer housing and pin may be connected to an external power source associated with the apparatus.

BRIEF DESCRIPTION OF THE SEVERAL VIEWS OF THE DRAWING(S)

DETAILED DESCRIPTION OF THE INVENTION

Figure 1:
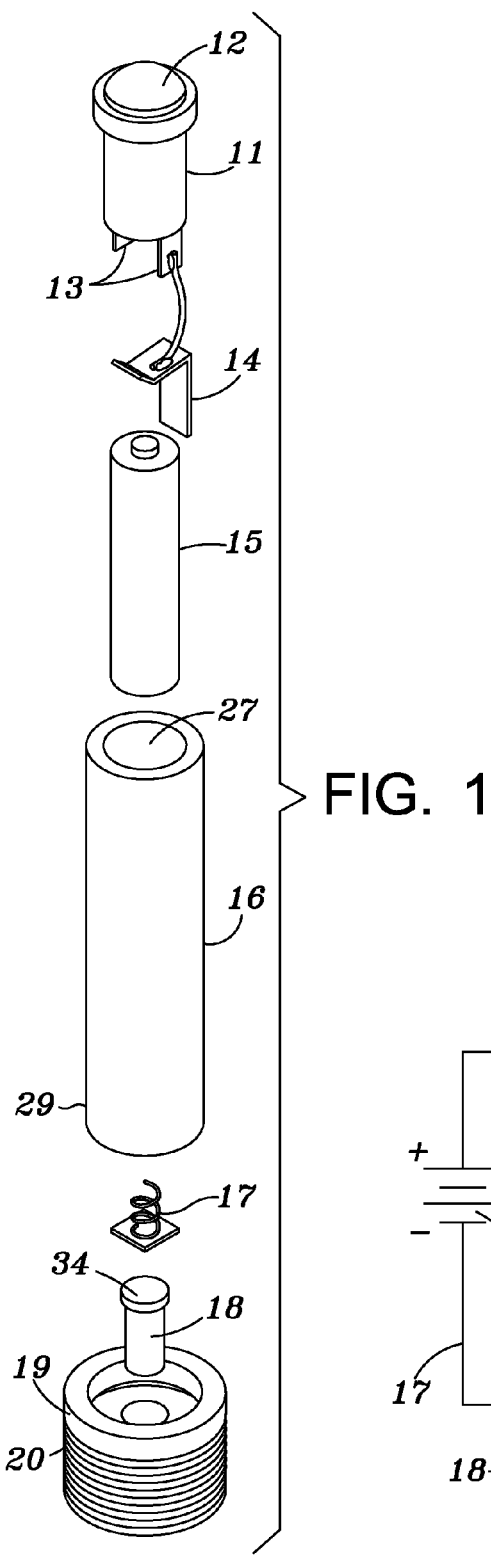
FIG. 1 is an exploded view of an embodiment of the inventions.
Figure 3:
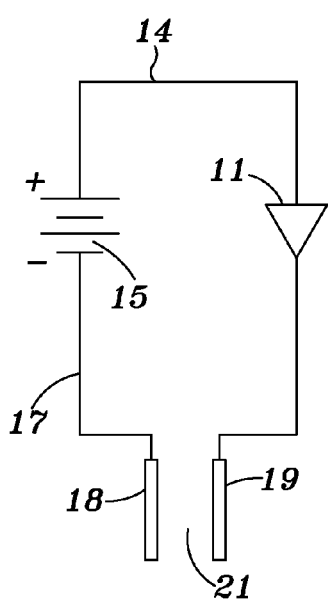
FIG. 3 is an electrical circuit suitable for carrying out the invention.

Referring to FIG. 1, an embodiment of the invention includes an outer generally cylindrical housing 16 having an interior bore 27. Outer housing 16 at its lower end 29 is connected to a cylindrical member 19 having interior bores at 31 and 32. A signal device such as an LED 11 is positioned within bore 27 of outer housing 16 at an upper end thereof. LED 11 includes two contacts 13. A battery which may be of the AA size is positioned within outer housing 16. A first battery contact 14 is electrically connected to a first contact 13 of LED display assembly 11 and to the positive terminal of battery 15. A second battery contact 17 is electrically connected to the negative terminal of battery 15 and also to pin 18 as shown in FIG. 3.

Figure 2:
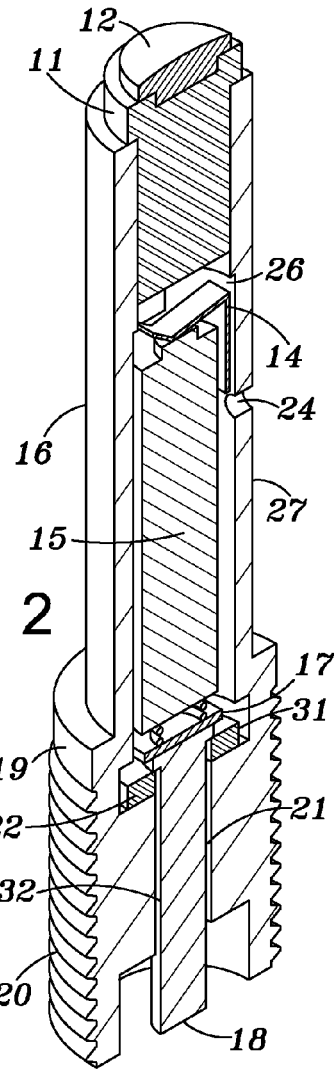
FIG. 2 is a cross-sectional view of the embodiment shown in FIG. 1.

A second contact 13 of LED display assembly is electrically connected to outer housing 16 which is electrically connected to cylindrical member 19. However, pin 18 is normally electrically isolated from member 19 by a non-conductive seal 22 shown in FIG. 2. There is an annular gap 32 between pin 18 and the internal bore 21 of cylindrical member 19. The outer surface of cylindrical member 19 is threaded at 20 so as to be secured within a lower section of the reservoir according to its particular use. For example, the reservoir may be an oil pan or a crank case.

From the forgoing it is apparent that the sensor as described above may be secured to the lower portion of a reservoir for normally non-conducting liquids such as oil or engine fuel. Should the reservoir become contaminated with a conduct fluid or material such as water, the water will settle to the bottom of the reservoir since it is heavier than oil or other fuels and enter the annular gap 32 between pin 18 and member 19. This will close the electrical circuit shown in FIG. 3 which causes signal device 11 to be activated.

An external power source may be used in lieu of battery 15 in which case it would be connected to housing 19 and pin 18 via electrical wires from the external power source.

Although the present invention has been described with respect to specific details, it is not intended that such details should be regarded as limitations on the scope of the invention, except to the extent that they are included in the accompanying claims.

We claim:

1. A sensor for detecting the presence of an electrically conductive material comprising:
   an electrically conductive outer housing having an internal bore extending therethrough;
   a signal device located at a first end portion of the outer housing;
   a cylindrical member having an internal bore extending therethrough located at a second end of said housing;
   an electrically conductive cylindrical pin located within the bore of the cylindrical member and electrically insulated from the cylindrical member, thereby forming an annual space between the pin and the cylindrical member,
   the pin and the cylindrical member adapted to be connected to a power source whereby when an electrically conductive material enters a space between the pin and the bore of the cylindrical member, it will complete an electrical circuit which will activate the signal device.

2. The sensor as claimed in claim 1 including a power source located within the outer housing.

3. The sensor as claimed in claim 1 including an external power source.

4. The sensor as claimed in claim 1 wherein the signal device is a light emitting diode.

5. The sensor of claim 1 wherein the cylindrical member has screw threads on an outer surface thereof.

* * * * *